United States Patent [19]
Vanderbilt

[11] Patent Number: 5,326,506
[45] Date of Patent: Jul. 5, 1994

[54] METHOD FOR MAKING A COMPOSITE INTRAOCULAR LENS

[75] Inventor: David P. Vanderbilt, St. Louis, Mo.

[73] Assignee: American Cyanamid Company, Wayne, N.J.

[21] Appl. No.: 10,373

[22] Filed: Jan. 28, 1993

Related U.S. Application Data

[62] Division of Ser. No. 634,919, Dec. 27, 1990, Pat. No. 5,217,491.

[51] Int. Cl.$^5$ ............................................. B29D 11/00
[52] U.S. Cl. ..................................... 264/1.7; 264/2.7; 623/6
[58] Field of Search ................... 264/1.7, 2.7; 623/6

[56] References Cited

U.S. PATENT DOCUMENTS

| | | | |
|---|---|---|---|
| 3,983,083 | 9/1976 | Kaetsu et al. | 526/240 |
| 4,093,361 | 6/1978 | Erickson et al. | 351/160 |
| 4,121,885 | 10/1978 | Erickson et al. | 351/177 |
| 4,556,998 | 12/1985 | Siepser | 623/6 |
| 4,615,702 | 10/1985 | Koziol et al. | 623/6 |
| 4,687,485 | 8/1987 | Lim et al. | 623/6 |
| 4,702,865 | 10/1987 | Koziol et al. | 264/17 |
| 4,718,906 | 1/1988 | Mackool | 623/6 |
| 4,764,169 | 8/1988 | Grendahl | 623/6 |
| 4,774,036 | 9/1988 | LeMaster et al. | 264/1.7 |
| 4,787,904 | 11/1988 | Severin et al. | 623/6 |
| 4,813,956 | 3/1989 | Gupta | 623/6 |
| 4,834,751 | 5/1989 | Knight et al. | 623/6 |
| 4,893,918 | 1/1990 | Sulc et al. | 351/160 |
| 4,961,746 | 10/1990 | Lim et al. | 264/1.7 |
| 4,978,354 | 12/1990 | Van Gent | 623/6 |
| 4,997,442 | 3/1991 | Barrett | 623/6 |
| 5,037,435 | 8/1991 | Chang et al. | 264/1.7 |
| 5,089,180 | 2/1992 | Dunks et al. | 264/1.7 |
| 5,182,053 | 1/1993 | Creasman et al. | 264/1.7 |

FOREIGN PATENT DOCUMENTS

| | | |
|---|---|---|
| 0099641 | 2/1984 | European Pat. Off. . |
| 0333348 | 9/1989 | European Pat. Off. . |

*Primary Examiner*—James Lowe
*Attorney, Agent, or Firm*—Brian R. Woodworth

[57] ABSTRACT

A method for making a composite intraocular lens having an optic portion and haptic portion. The method includes the steps of forming a core of a high refractive material suitable for use as an intraocular lens optic, swelling the core, placing a polymerizable material capable of forming an intraocular lens haptic about the core, and polymerizing the polymerizable material. The method further includes the step of machining the resulting composite rod in order to form a composite intraocular lens having an optic portion and a haptic portion.

14 Claims, 2 Drawing Sheets

METHOD FOR MAKING A COMPOSITE INTRAOCULAR LENS

This is a divisional of co-pending application Ser. No. 07/634,919 filed on Dec. 27, 1990, now U.S. Pat. No. 5,217,491 issued Jun. 8, 1993.

BACKGROUND OF THE INVENTION

This invention relates to intraocular lenses and, more particularly, to composite intraocular lenses which are foldable so as to be insertable through a small incision of approximately 3 to 4 millimeters (mm).

The natural eye, in humans and most, if not all, animals, contains a lens located internally which focuses images on the retina. Either through disease or other naturally occurring processes, or mutations, the lens may fail to function properly. For instance, the lens, by mutation, may have been eliminated from the eye during its formation at birth. Or the lens may be cloudy at birth, or become cloudy over time. This clouding of the lens is known as a cataract, which inhibits the transmission of visual information through the lens to the retina.

The removal of diseased natural lenses has, prior to the advent of intraocular lenses, required a large incision into the eye at the junction of the cornea and the sclera in order to remove the lens. The healing time in such an operation was substantial and the pain was severe. No lens was inserted in place of the natural lens and eyeglasses or external-type contact lenses were employed to help correct restored vision to the patient.

The advent of intraocular lenses, along with the instruments needed to insert them, was a helpful innovation. Surgical incisions were still relatively large, on the order of 10–14 millimeters (mm), and healing time remained substantial; however, this incision length was required for the cataract removal operation, whereas intraocular lens implants required only a 6 or 7 mm incision for their insertion.

More recently, the cataract extraction operation performed by ultrasonic destruction and suction (phacoemulsification) has been developed and allows the removal of the cataract through an incision as small as 3 mm. However, presently this incision must then be enlarged from 5 to 7 mm for insertion of the intraocular lens implant. Experience has shown that the longer the incision, the longer it takes to heal, the greater the danger of rupture of the incision postoperatively, and the greater the danger that scar tissue, which forms during the healing process, will interfere with the patient's vision. Furthermore, the longer the incision and resultant scar, the greater the danger that post-operative astigmatism will occur due to uncontrolled healing of the eye tissue. It is therefore desirable to develop an intraocular lens implant capable of being inserted through an incision not greater than that which is necessary for cataract extraction, i.e., 3 mm.

One proposal for reducing the length of the incision requires the use of a very soft material for the lens, soft enough to permit the lens to be folded, inserted through the incision, and released. One such material is silicone; however, a lens made from silicone is so extremely soft that, as a result, when the lens and its haptics are permitted to unfold in the eye, the almost jelly-like softness of the lens makes it difficult for the surgeon to properly position the lens in the eye. The jelly-like softness of the silicone lens does not provide sufficient rigidity for the lens after insertion and, as the lens moves about, the optical integrity of the lens may thereafter be affected. In addition, the jelly-like softness of this lens makes it difficult to insert, unfold and position the lens via its haptics in the posterior chamber of the eye. It is the posterior chamber into which most intraocular lenses are placed, as it is behind the iris, like the natural lens it replaces.

Furthermore, there is often a compressive force exerted on the lens by ocular structures following surgery, and these can, and have resulted in deformation of the soft lens and haptics to cause reduced vision in the patent. One of these potentially compressing structures, the lens capsule, surrounds the human lens entirely. It is common practice for the lens implant to be intentionally placed within the capsule following the removal of the cloudy lens or cataract from within the capsule. This is widely accepted to be a preferred method for securing the lens implant as great stability is afforded the implant, and its position within the capsule prevents the implant from contacting more delicate ocular structures. Silicone lenses are, however, not recommended for this type of placement within the capsule as the compressive forces from the capsule can produce lens distortion and reduced vision following surgery.

Another material, or combination of materials, which could be used for a soft, foldable intraocular lens would be a poly(hydroxyethyl methacrylate) or pHEMA or other soft acrylic material, and a rigidizing structure on, or in, the lens, made from a relatively hard plastic such as poly(methyl methacrylate) or PMMA such as disclosed in U.S. Pat. No. 4,718,906. However, the lenses shown in this patent are manufactured by combining these two materials by various methods such as embedding one material in the other, or concurrent extrusion processes, or by solidifying the soft material about the hard material.

Furthermore, U.S. Pat. No. 4,718,906 does not disclose a method of polymerizing the soft pHEMA and hard PMMA materials to a satisfactory manner. These two polymers are dissimilar and an attempt to simply polymerize the PMMA to the pHEMA will result in an intraocular lens having an unstable bond which is easily broken. All of the methods disclosed in U.S. Pat. No. 4,718,906 will provide a two- or multiple-piece lens which is ultimately unsatisfactory for use in the eye.

U.S. Pat. No. 4,764,169 to Grendahl discloses an intraocular lens including a small, hard inner lens optic and a soft, pliable skirt surrounding the lens optic. The lens optic material is a relatively hard material such as PMMA, polysulfonce, polycarbonate, or like biocompatible material. The soft, pliable skirt is a silicone, hydrogel or like material. However, the specification fails to disclose how a soft hydrogel material is cast or otherwise polymerized to the central hard PMMA material of the lens optic. Furthermore, Applicant has discovered that while it is fairly easy to cast or polymerize HEMA to form a soft hydrogel around a hard PMMA core and obtain a good said bond therebetween, that the opposite procedure of casting a hard PMMA ring around a soft pHEMA core does not produce a good bond.

U.S. Pat. Nos. 4,093,361 and 4,121,885 to Erickson et al. disclose a composite contact lens and method of manufacture wherein the contact lens has a hard center lens portion and a soft peripheral skirt. The skirt portion being a hydrophilic, water-swellable polymer. An inert, water-soluble substance is added to the monomer feed used to form the skirt portion. After curing, the composite contact lens is hydrated, and the water-soluble substance is leached out, thus eliminating any distortions and/or stresses in the skirt portion. However, the material of the hard center and soft skirt are compatible such that they will properly bond together.

U.S. Pat. No. 4,687,485 to Lim et al, and currently assigned to the same assignee as the present invention, further discloses a method of joining together various materials to form a composite intraocular lens wherein the optical portion of the lens is manufactured out of PMMA and the outermost portion of the haptics or legs includes a region of compressible material (i.e., various HEMA copolymers). The compressible regions on the haptics provided a lens which alleviated discomfort and/or trauma to the eye tissues at the point of contact between the patient's eye and the compressible region of the intraocular lens haptic.

It is one primary object of the invention to provide a one-piece, small-incision intraocular lens having a soft, foldable optic portion and a hard, stiff haptic portion.

Another primary object of this invention is to provide a novel polymer composition for an intraocular lens utilizing two dissimilar polymeric materials to form a one-piece intraocular lens.

It is another object of this invention to provide a one-piece intraocular lens having a soft, foldable optic portion and a hard, stiff haptic portion while providing excellent biocompatibility with the patient's eye.

It is an alternate object of the invention to provide a one-piece intraocular lens having a soft, foldable optic portion and a hard, stiff haptic portion wherein the stiff haptic portion has a further soft material at its terminus to protect the eye tissues at the point of contact without sacrificing the lens positioning properties of stiff haptics.

It is another object of this invention to provide a method of making a one-piece intraocular lens utilizing two dissimilar polymeric materials wherein one polymeric material is soft enough to fold and the second polymeric material providing a stiffness sufficient to properly hold the intraocular lens in place within a patient's eye.

BRIEF DESCRIPTION OF THE INVENTION

The new intraocular lens of the present invention is a one-piece composite lens having a soft, foldable central optic region and a hard, non-foldable outer peripheral region making up the haptics or legs of the intraocular lens. The soft, central optic portion of the lens is typically manufactured from a material capable of being folded so that the intraocular lens can be inserted through a small incision on the order of 3 to 4 mm. The hard haptic portion of the lens provides support for the lens in the eye after insertion and unfolding of the lens. The relatively rigid plastic lends support to the entire lens structure after its insertion into the posterior chamber of the eye, and tends to help stabilize the position of the lens after insertion and the closure of the incision.

The invention further describes a method of strongly joining together two dissimilar polymer materials so that a one-piece foldable intraocular lens may be lathed from the composite material disc having two or more different polymer regions.

A preferred material of the soft optical region being a poly(hydroxyethyl methacrylate) or pHEMA or a copolymer thereof such as HEMA and 6-hydroxyhexyl methacrylate (HOHEXMA) or p(HEMA-co-HOHEXMA). The preferred material of the hard haptic region being made from a relatively hard plastic, such as (polymethyl methacrylate) or PMMA, or a copolymer thereof.

The method of the present invention comprises lathe-cutting discs from a rod into the intraocular lens of the present inventions. The discs can be made by a procedure which begins with polymerizing in a tubular or cylindrical mold a liquid mixture of initiator and monomer or comonomers such as HEMA or HEMA and HOHEXMA or other acrylic monomers for forming an optically clear soft lens body. As is known in the art, it may be desirable to add a crosslinking material and ultraviolet absorbing compounds directly to this mixture prior to polymerization so as to be incorporated into the resultant polymer. The polymer rods produced by these means are then lathe cut, or centerless ground, to the diameter of the desired lens body.

This core rod is then centered in a larger diameter tubular mold and the polymerizable liquid that, upon curing, will comprise the hard, outer polymer segment is placed in contact with the rod.

In cases where the polymerizable outer liquid does not soften, or penetrate the core material (i.e., pHEMA core with MMA sheath), no bonding at the interface will take place. In these situations, bonding can be effected by pre-swelling the core material with a solvent or swelling agent that is also miscible with the polymerizable outer liquid and can itself be polymerized. Alternatively, in some cases, the polymerizable swelling agent for the core polymer may be added directly to the polymerizable outer liquid.

A third method to accomplish bonding is to alter the composition of the core rod so that the polymerizable outer liquid will then swell and penetrate the core. This can be accomplished by adding a comonomer to the core monomer feed that will ultimately become the soft core rod, thus rendering the resultant copolymer more susceptible to swelling by the polymerizable outer liquid that will ultimately become the hard, stiff outer sheath.

The resultant composite rod is then lathe cut on centerless ground to a diameter slightly larger than the length of the whole intraocular lens. The composite rod is then sawed or otherwise cut into discs of uniform thickness suitable for lathe cutting and machine milling in the conventional manner into an intraocular lens of the present invention having a soft, foldable optic portion and hard, stiff haptics for proper retention in the eye.

An alternate embodiment of the invention provides a one-piece composite lens having a soft, foldable central optic region and hard, non-foldable outer haptic portion wherein the haptics have a further soft region at their outer terminus. The soft material region on the haptics is provided so as to cushion the point of contact between the patient's eye tissue and the haptic of the intraocular lens.

BRIEF DESCRIPTION OF THE DRAWINGS

These and other features, aspects, and advantages of the present invention will become more apparent when considered with respect to the following description, appended claims, and accompanying drawings, wherein:

DESCRIPTION OF THE PREFERRED EMBODIMENTS

Figure 1:
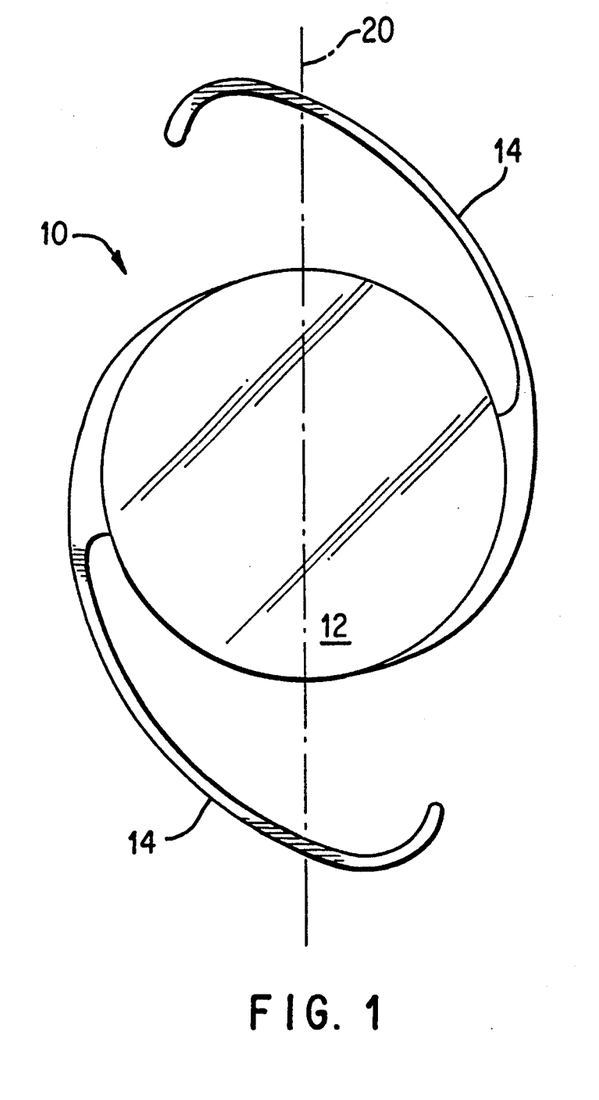
FIG. 1 is a plan view of an exemplary composite intraocular lens including a central, soft, foldable optic portion and hard, stiff haptics provided in accordance with the practice of this invention.
Figure 2:
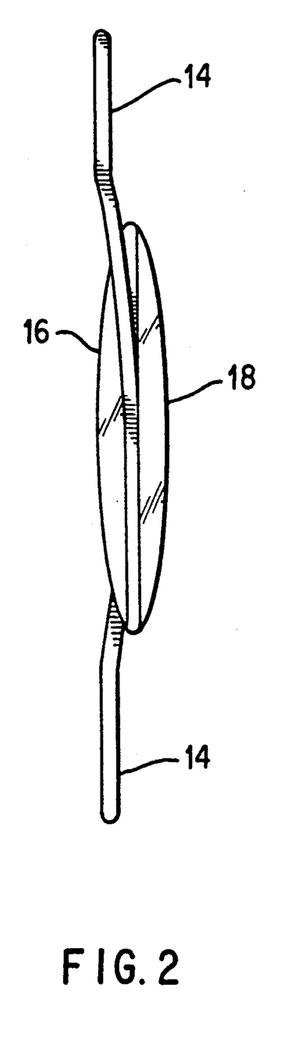
FIG. 2 is a side view of the exemplary composite intraocular lens of FIG. 1.

Referring to FIGS. 1 and 2, an embodiment of an intraocular lens in accordance with the present invention is illustrated in a plan view (FIG. 1) and a side view (FIG. 2). Numeral 10 denotes the intraocular lens in general and 12 refers to the lens optic portion which is approximately 6 mm in diameter prior to hydration. The 6 mm diameter is fairly standard in the art, and is generally chosen to cover the pupil in its fully dilated state under naturally occurring conditions. However, other sizes are possible and this invention is in no way limited to any particular diameter or size. Furthermore, it is not necessary that the lens optic portion be circular; it could also be oval, square or any other shape as is desired.

The intraocular lens 10 comprises one or more non-optical haptic or leg components 14 extending away from the outermost peripheral surface of optic portion 12. The haptic components are useful for supporting the lens within the posterior chamber of the eye. Although the optic portion 12 of lens 10, shown in FIG. 2, is a bi-convex lens, (i.e., it has convex surfaces 16 and 18 on both its front and rear sides, respectively), lenses having any desired design configuration can be provided. Further, although two haptics 14 are shown, fewer or more haptics can be used as desired and the haptics can have configurations other than the configurations of the haptics shown in the various embodiments of the invention.

The intraocular lens of the present invention is a one-piece composite lens 10 having a soft foldable central optic portion 12 and stiffer, harder non-foldable haptic or leg components 14 extending outwardly from the outermost peripheral surface of optic portion 12. The lens of FIG. 1 may be folded prior to insertion by small, thin forceps of the type typically used by ophthalmic surgeons. Folding using the forceps occurs along center line 20 with the soft central portion 12 folding approximately in half to allow the lens to be inserted through a small incision of about 3 to 4 mm.

After the lens is in the targeted location, it is released to unfold. The material selected for central optic portion 12 is made of a physiologically inert soft polymeric material which is capable of providing a clear, transparent, refractive lens body even after folding and unfolding. After the lens is unfolded, the forceps are extracted by the surgeon through the incision and a positioning tool is used to properly locate the intraocular lens in the posterior chamber of the patient's eye.

The preferred material of the soft optic portion 12 being a poly(hydroxyethyl methacrylate) or pHEMA or a copolymer thereof such as HEMA and 6-hydroxyhexyl methacrylate (HOHEXMA) with polyfunctional crosslinking agents such as ethylene glycol dimethacrylate (EGDMA) or 1,6-hexanediol dimethacrylate (HDDM). Other suitable materials for optic portion 12 are polymers of 2, 3-dihydroxypropyl methacrylate, and other hydrophilic amides and hydroxylated monomers and copolymers such as:

HEMA/N-vinylpyrrolidone
2,3-dihydroxypropyl methacrylate/methyl methacrylate
HEMA/N-vinylpyrrolidone/methyl methacrylate
HEMA/methacrylic acid
HEMA/2-ethoxyethyl methacrylate
HEMA/methacrylic acid/isobutyl methacrylate
hydroxypropyl methacrylamide/methyl methacrylate
HEMA/n-butyl methacrylate
HEMA/n-hexyl methacrylate
HEMA/n-octyl methacrylate
HEMA/hydroxyoctyl methacrylate
dimethyl acrylamide/diethyl acrylamide
HEMA/n-hexyl acrylate
HEMA/hydroxypropyl methacrylate Although acrylic hydrogels are the preferred materials for the foldable optic portion, the methods described herein can also be applied to join hard polymers such as PMMA to non-water-containing, soft polymers such as acrylic polymers and copolymers and silicones that have glass transition temperatures ($T_g$'s) below physiologic temperatures.

The term "soft" in the context of this application, is used to describe a polymeric material that has a $T_g$ of less than 37° C. when in the physiologic environment. Thus, pHEMA, which in its xerogel (dehydrated) form has a high $T_g$ (~100° C.), is classified as a soft material because, after hydration, the $T_g$ is <37° C.

Examples of non-water-containing, low $T_g$ acrylic homopolymers are given below.

|  | $T_g$, °C. |
| --- | --- |
| poly (ethyl acrylate) | −24 |
| poly (propyl acrylate) | −45 |
| poly (n-butyl acrylate) | −55 |
| poly (isobutyl acrylate) | −43 |
| poly (hexyl acrylate) | −57 |
| poly (2-ethylhexyl acrylate) | −50 |
| poly (2-ethoxyethyl acrylate) | −50 |
| poly (dodecyl acrylate) | −30 |
| poly (n-octyl methacrylate) | −20 |
| poly (n-decyl methacrylate) | −60 |
| poly (dodecyl methacrylate) | −65 |
| poly (tetradecyl methacrylate) | −72 |
| poly (hexadecyl methacrylate) | −72 |
| poly (octadecyl methacrylate) | −100 |

It should be pointed out that the monomers used to prepare the above homopolymers can also be used to form copolymers with other acrylic monomers to form resultant materials with intermediate values of $T_g$. We define the term copolymer for the purposes of this application to mean the polymer formed from 2 or more different polymerizable monomers.

The approximate value of $T_g$ for a copolymer can be calculated from knowledge of the weight fraction (W) of each monomer type and the $T_g$ (°K.) of each homopolymer by:

$$\frac{1}{T_g} = \frac{W_1}{T_{g1}} + \frac{W_2}{T_{g2}} + \ldots \frac{W_n}{T_{gn}}$$

The material of the hard, stiff haptic portions 14 being made from a relatively hard plastic such as poly(methyl methacrylate) or PMMA, or a copolymer thereof.

The invention further describes a method of strongly joining together two dissimilar polymer materials such that a one-piece foldable intraocular lens may be machined from a composite material disc. These discs can be made by a procedure which begins with polymerizing in a tubular or cylindrical mold a liquid mixture of initiator and monomer, comonomers or copolymer thereof as previously described for forming an optically clear, soft, foldable lens optic portion 12.

It may be necessary to also add crosslinking agents such as ethylene glycol dimethacrylate (EGDMA), triethylene glycol dimethacrylate (TEGDMA), or 1,6-hexanediol dimethacrylate (HDDM) or other bifunctional and polyfunctional monomers as is well known in the art in amounts in the range of 0-10% to give the resultant copolymer dimensional stability. It may also be necessary to add ultraviolet (UV) absorbing compounds in with the lens body monomers prior to polymerization for incorporation into the resultant polymer as is well known in the art. The UV absorber should preferably be capable of polymerization into the lens matrix so as to resist extraction under physiologic conditions.

The polymer rods produced by these means are then lathe cut to the prehydrated diameter or shape so as to obtain the desired lens optic portion 12. The resultant rods are then precisely mounted in the center of a cylindrical tubular mold and mixtures of initiator and monomers, previously described as suitable for forming the polymer of the hard, stiff haptic material are added and polymerized to form a cylindrical ring around the rod of the polymer used to form the lens optic portion 12. However, it is also possible to mount the polymer rods of the lens optic portion 12 off center such than an intraocular lens of a different shape or configuration may be obtained such as an oval or square optic portion or the like.

It may also be desirable to provide a physiological dye into the surrounding ring mixture so that the haptics 14 will be colored to allow the intraocular lens to be easily seen once placed into the patient's eye by the surgeon. Color can be imparted by incorporating into the surrounding ring mixture any physiologically compatible dye such as D & C Green #6, which, despite its name, provides a blue color into the haptic portion of the intraocular lens.

It may be necessary to place a solvent or swelling agent in contact with the material of the central optic portion (e.g. pHEMA rod) before polymerizing the surrounding cylindrical PMMA ring portion to the rod so that a good bond therebetween will be obtained. This can be accomplished by using a swelling agent which will be miscible with both the material of the cylindrical ring portion and the core material and is itself polymerizable. The rod can be immersed into the solvent or swelling agent for a predetermined period of time and then removed and rinsed before being polymerized to the material of the surrounding ring portion or the swelling agent can be mixed in the material of the surrounding ring portion and be cured to the rod in conjunction with the material of the cylindrical ring portion.

As discussed above, the preferred material of the central optic portion is an acrylic hydrogel pHEMA or a copolymer thereof. The preferred polymerizable solvent or swelling agent miscible with the pHEMA is HEMA in most of the examples. The material of the surrounding cylindrical ring portion is PMMA, such that the HEMA (swelling agent) is miscible with the MMA monomer.

An explanation of how this provides a good bond, or adhesion, between the two dissimilar polymer layers is that the pHEMA or pHEMA copolymer rod core portion is swelled on its surface by the HEMA solvent or swelling agent. The MMA monomer of the cylindrical ring portion can then diffuse into this softened layer because the HEMA and MMA are miscible and, upon polymerization of the MMA, an interpenetrating polymer network forms at the interface. This interlocked network of pHEMA and PMMA chains provide a good strong mechanical bond between the two materials, even after the pHEMA portion is hydrated.

The resultant composite material rod is then lathe cut or ground to a radius 1.0-3.0 mm more than the distance from the center of the lens body to the furthest edge of the legs. This rod is then sawed or otherwise cut into discs of uniform thickness suitable for lathe cutting and machine milling in the conventional manner into the intraocular lens of the present invention.

Figures 3, 4:
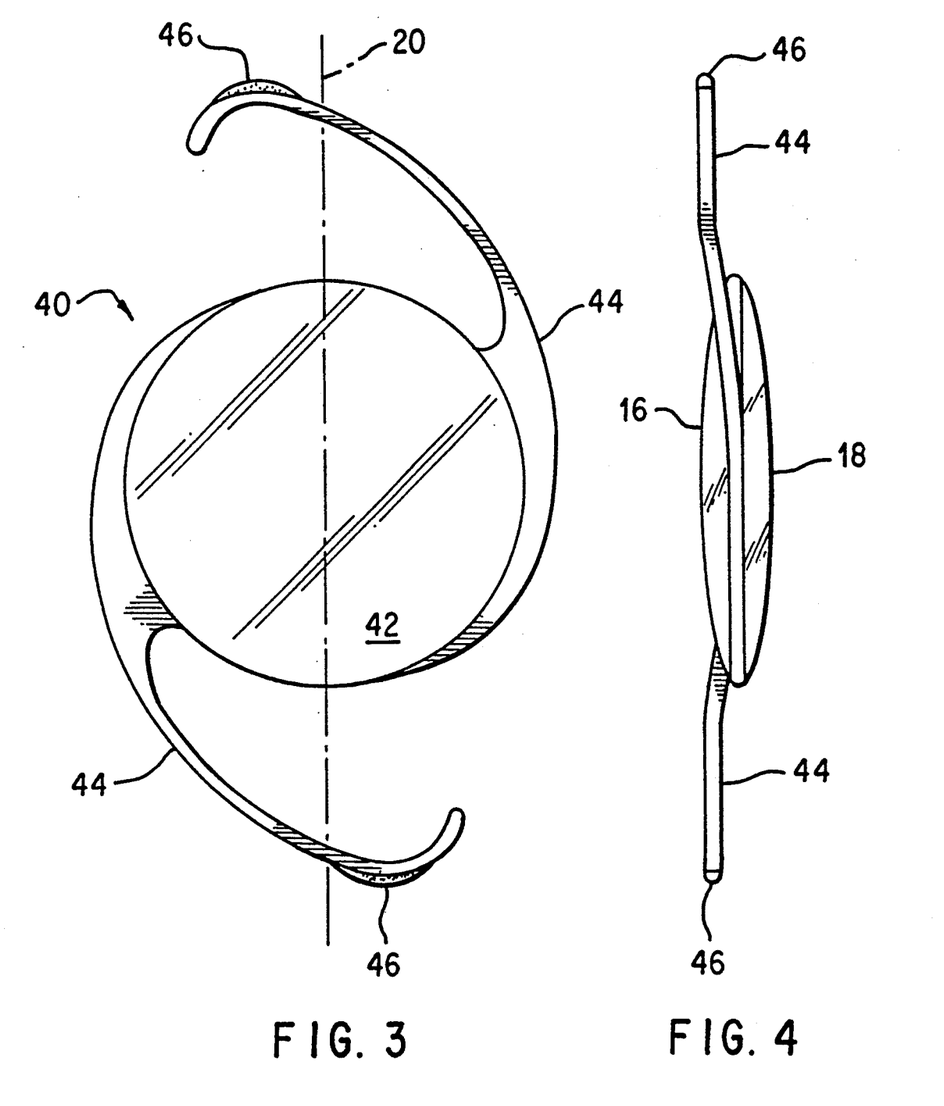
FIG. 3 is a plan view of another embodiment of the invention illustrating a composite lens having a different configuration of soft and hard material portions of the lens.
FIG. 4 is a side view of the embodiment shown in FIG. 3.

A second embodiment of the invention is shown in FIG. 3 and 4 wherein an intraocular lens 40 is illustrated. The lens 40 includes a soft, foldable optic portion 42 and stiffer, harder non-foldable haptic or leg portions 44 extending outwardly from the outermost peripheral surface of optic portion 42. Each leg 44 includes a region near its outer end which contacts the eye tissue designated as 46. It is desirable that regions 46 of the leg portions 44 be manufactured out of a soft, compressible material which will not harm the delicate eye tissue which it will contact when positioned within a patient's eye.

A satisfactory material for use in regions 46 of haptics 44 is the pHEMA or copolymer thereof used for the central optic portion as previously described. To form an integral intraocular lens having a soft, foldable central optic portion and hard, stiff haptic regions including compressible zones 46 on haptics 44, the lens body or optic portion and cylindrical ring portion are polymerized in a tube by the methods described above and then lathe cut to a radius 0.1-1.0 mm less than the distance from the center of the lens body to the interface between the compressible material 46 and the eye tissue which the compressible material will contact. The resultant rods are then precisely mounted in the center of a second cylindrical tubular mold and mixtures of initiator and monomers, previously described as suitable for forming the polymer of the compressible material 46, are added and polymerized to form a second cylindrical ring around the central rod and first cylindrical ring used to form the lens body and most or all of the legs of the lens. The resultant rod is then lathe cut to a radius 1.0-3.0 mm more than the distance from the center of the lens body to the farthest edge of the legs. This rod is then sawed or otherwise cut into discs of uniform thickness, suitable for lathe cutting and machine milling in the conventional manner into the intraocular lens of the present invention, as previously described.

It is felt that the invention is best described by reference to the following examples which illustrate the various methods of manufacturing an exemplified intraocular lens. The following examples are representative of laboratory results demonstrating both unsuccessful and successful formation of composite intraocular lenses from two dissimilar materials as described above.

EXAMPLE I

Three pHEMA rods approximately 2.5 inches long by 0.4 inches in diameter, crosslinked with 1% by weight ethylene glycol dimethacrylate (EGDMA), and three pHEMA rods crosslinked with 4% by weight triethylene glycol dimethacrylate (TEGDMA) of similar size were centered by means of Teflon spacers inside polypropylene test tubes (approximately 3.5 inches long by 0.75 inches inside diameter). To each mold was added a solution of methyl methacrylate (MMA, 100 parts by weight), EGDMA (1.0 parts by weight), 2,2-azobisisobutyronitrile (AIBN, 0.0875 parts by weight), and D & C Green No. 6 (0.10 parts by weight). The molds were stoppered shut with flanged Teflon plugs having a Viton O-ring around the circumference of the plug to provide a good seal. The tubes were suspended in a water bath held at 40° C. for 47 hours and the bath was subsequently ramped to 60° C. for 20 hours, removed from the bath, and further cured in a forced-air oven at 100° C. for 20 hours. This is referred to as the standard cure method. After cooling, the cured rods were removed from the molds and sliced into discs (1 mm to 3 mm in thickness). The incorporation of the blue dye, (D & C Green No. 6) in the sheath or surrounding cylindrical ring solution, allowed for easy inspection of the core/sheath or central optic portion/haptic portion interface. In this and all examples, no blue dye was seen to penetrate into the pHEMA core. Furthermore, the colorless core could be readily pushed out of the composite disc indicating that the liquid MMA did not penetrate or diffuse into the pHEMA core to any significant extent prior to polymerizinig. Therefore, a composite intraocular lens manufactured according to this example would not exemplify the teachings of the present invention because the part the lens comprising the sheath material (the legs or haptics 14 and 44 of FIGS. 1 and 3, respectively) would easily fall off or break away from the central optic region of the lens.

EXAMPLE II

The experiment described in Example I was repeated using two core rods of pHEMA and two core rods of a copolymer of HEMA and MMA, or p(HEMA-co-MMA), at a 50/50 mol ratio and two core rods of a copolymer p(HEMA-co-MMA) at a 75/25 mol ratio of HEMA to MMA. No crosslinker was present in any of the core rods of this example. These rods were centered in a mold as described in Example I, and to each mold was added a solution of MMA (100 parts by weight), EGDMA (1.0 parts), AIBN (0.05 parts), and D & C Green No. 6 (0.10 parts). The rods were cured using the standard cure method as in Example I. The colorless center core could be pushed out of the composite disc in the case of the pHEMA/MMA and 75/25 p(HEMA-co-MMA)/MMA composite discs, but not in the case of the discs sliced from the 50/50 p(HEMA-co-MMA)/-MMA composite rods. However, after these lathed discs were hydrated in water, the center core portion could be easily pushed out or eliminated from the sheath portion. Therefore, a composite intraocular lens manufactured according to this example would not perform in accordance with the teachings of the present invention.

EXAMPLE III

The experiment described in Example I was repeated using both pHEMA and 75/25 p(HEMA-co-MMA) central core rods containing no crosslinker. In this example, the sheath casting solutions that were placed in the molds surrounding the core rods were solutions of MMA and HEMA at 90/10 and 80/20 mol ratios of MMA to HEMA (no added crosslinker). The composite rods were cured in the standard cure method of Example I. The cured rods were sliced into discs and, from the discs, intraocular lens were made using standard lathing and milling techniques having a central soft optic portion and harder, stiffer blue haptic portions. The lenses were hydrated in distilled water and the blue haptics were found to be securely joined to the clear optic portion of the lens in the case of the 75/25 p(HEMA-co-MMA) core rods, but not in the case of the pHEMA core rods.

EXAMPLE IV

Core rods (0.40 inch diameter) made from the pHEMA of Examples I and II, crosslinked with 1 mol percent TEGDMA, were immersed in distilled HEMA at room temperature and the average increase in diameter of the rods was measured with calipers at various intervals as shown in Table I below.

TABLE 1

| Immersion Time (in days) | Diameter Increase (inches) |
| --- | --- |
| 1 | 0.003 |
| 2 | 0.005 |
| 22 | 0.010 |

The 22-day-swelled rods were subsequently made into composite rods with a PMMA sheath including an EGDMA (1.0 part) crosslinker, AIBN (0.05 parts) initiator, and D & C Green No. 6 dye (0.10 parts). The cured rods were sliced into discs and hydrated as described previously. The blue PMMA haptic portion was found to adhere strongly to the colorless pHEMA central optic portion as determined by pull tests. No failures occurred at the pHEMA/PMMA interface.

EXAMPLE V

This experiment was conducted to determine the effect of core surface area on adherence of the sheath polymeric material. Copolymer core rods, made from a 70/30 mol ratio of HEMA and 6-hydroxyhexyl methacrylate (HOHEXMA) or p(HEMA-co-HOHEXMA) and crosslinked with 3 mol percent of triethylene glycol dimethacrylate (TEGDMA) plus 1,6-hexanediol dimethacrylate, were turned on a lathe to a diameter of 0.375 inches. One of the lathed cores was allowed to swell in water overnight and was subsequently freeze-dried. A second lathed core was wiped with an acetone-damp cloth prior to being centered in the mold. A third core was used as cast (not lathed). MMA (100 parts by weight) containing EGDMA (1.0 part), AIBN (0.05 parts), and D & C Green No. 6 (0.10 parts) were cast around each core as in Example I. The cure conditions were similar to those of Example I. The cured rods were sliced into discs 1-3 mm thick and immersed in water to test the integrity of the interface. The two polymeric zones were strongly bonded together in all three cases.

EXAMPLE VI

Three 70/30 mol ratio p(HEMA-co-HOHEXMA) core rods that had been previously lathed to 0.375 inch diameter were allowed to soak in distilled HEMA for 22 hours at room temperature. The excess HEMA was blotted off and the cores were centered in polypropylene test tubes using polypropylene spacers as described in Example I. A solution of MMA (100 parts by weight), EGDMA (1 part), AIBN (0.05 parts), and D & C Green No. 6 (0.10 parts) was poured around the cores and the sealed molds were cured in a similar fashion to Example 1. The cured rods were turned down on a lathe to 16.4 mm diameter and sliced into 3 mm thick discs. The discs were checked for concentricity and those discs having a clear, central optic portion perfectly centered in the composite disc were made into one-piece composite intraocular lenses of a design similar to FIGS. 1 and 2. In hydrated form, the lenses could be folded repeatedly without damaging the clear, foldable optic portion or the colored, non-foldable haptic portions of the lens. Pull or tensile tests (discussed below) established that the PMMA haptic region was strongly affixed to the hydrogel core.

EXAMPLE VII

Example VI was repeated, however, in this example the 70/30 mol ratio p(HEMA-co-HOHEXMA) core rods were allowed to soak in distilled HEMA for 48 hours at room temperature prior to casting in the MMA solution of Example V. The rods were cured in both the standard way as shown in Example I and in an accelerated manner wherein the tubes were suspended in a water bath being ramped from 41° C. to 61° C. for 3 hours and then held at 61° for 24 hours. The tubes were removed from the bath and further cured in a forced-air oven at 113° C. for 38 hours. One core rod was cast into a composite using a sheath solution of MMA/HEMA (100 parts by weight, 95/5 mol ratio), EGDMA (1 part), AIBN (0.05 parts) and D & C Green No. 6 (0.10 parts) under the accelerated cure condition discussed above. The cured rods were machined into one-piece intraocular lenses as shown in FIGS. 1 and 2 and, subsequently, hydrated. No qualitative differences could be seen in the strength of the interface between the rods cured under the standard or accelerated conditions in the cases wherein the sheath solution was the MMA solution of Example V. However, failure at the interface was noted in blanks cut from the rod wherein the sheath solution was the 95/5 mol ratio MMA/HEMA.

EXAMPLE VIII

Three 70/30 mol ratio p(HEMA-co-HOHEXMA) core rods were lathed to 0.236 inch diameter (6.0 mm). These rods were not preswelled. The rods were centered in Pyrex molds. A sheath solution of 100 parts MMA, 1.0 parts EGDMA, 0.05 parts AIBN, and 0.10 parts D & C Green No. 6 was poured into the mold which was then sealed as discussed above. The rods were cured in accordance with this accelerated method as described in Example VI. The cured rods were sliced into lens blanks. Composite intraocular lenses having a 6 mm diameter central optic portion were fashioned from the lens blanks as is well known in the art. The lenses were hydrated and the strength of the hydrogel/PMMA interface was found to be strong.

Table 2 below depicts the results of Examples I through VIII:

TABLE 2

| EXAMPLE NO. | STRONG BOND OBTAINED | CORE COMPOSITION | PRESWELLING CONDITIONS | SHEATH COMPONENTS[a] | CURE CONDITION |
|---|---|---|---|---|---|
| 1 | No | pHEMA[b] | None | MMA[b,c] | Standard Method |
|   | No | pHEMA[d] | None | MMA[b,c] | Standard Method |
| 2 | No | pHEMA | None | MMA[b,e] | Standard Method |
|   | No | p(HEMA-co-MMA) (50/50) | None | MMA[b,e] | Standard Method |
|   | No | p(HEMA-co-MMA) (75/25) | None | MMA[b,e] | Standard Method |
| 3 | No | pHEMA | None | MMA/HEMA[e] (90/10) | Standard Method |
|   | Yes | p(HEMA-co-MMA) (75/25) | None | MMA/HEMA[e] (90/10) | Standard Method |
|   | No | pHEMA | None | MMA/HEMA[e] (80/20) | Standard Method |
|   | Yes | p(HEMA-co-MMA) (75/25) | None | MMA/HEMA[e] (80/20) | Standard Method |
| 4 | Yes | pHEMA[g] | HEMA, RT 22 days | MMA[b,e] | Accelerated Method |
|   | Yes | pHEMA[g] | HEMA, RT 22 days | MMA[b,e] | Standard Method |
| 5 | Yes | p(HEMA-co-HOHEXMA)[f] (70/30) (lathed) | None | MMA[b,e] | Standard Method |
|   | Yes | p(HEMA-co-HOHEXMA)[f] (70/30) (freeze-dried) | None | MMA[b,e] | Standard Method |
|   | Yes | p(HEMA-co-HOHEXMA)[f] (70/30) (cast) | None | MMA[b,e] | Standard Method |
| 6 | Yes | p(HEMA-co-HOHEXMA)[f] (70/30) | room temp. HEMA, RT 22 hours | MMA[b,e] | Standard Method |
| 7 | Yes | p(HEMA-co-HOHEXMA)[f] (70/30) | HEMA, RT 48 h | MMA[b,e] | Accelerated Method |
|   | Yes | p(HEMA-co-HOHEXMA)[f] (70/30) | HEMA, RT 48 h | MMA/HEMA[b,e] (95/5) | Accelerated Method |
|   | Yes | p(HEMA-co-HOHEXMA)[f] (70/30) | HEMA, RT 48 h | MMA[b,e] | Standard Method |
| 8 | Yes | p(HEMA-co-HOHEXMA)[f] (70/30) | None | MMA[b,e] | Accelerated Method |

[a] All sheath solutions contained 0.10 wt % D & C Green No. 6
[b] Ethylene glycol dimethacrylate (EGDMA), 1.0 wt %
[c] AIBN, 0.0875 wt %
[d] triethylene glycol dimethacrylate (TEGDMA), 4.0 wt %
[e] AIBN, 0.05 wt %
[f] TEGDMA + 1,6-hexanediol dimethacrylate, 3.0 mol %
[g] TEGMA, 1.0 mol %

EXAMPLE IX
TENSILE TEST

Copolymer core rods were prepared from 5 different mol ratios of HEMA to HOHEXMA; 70/30, 75/25, 80/20, 85/15, and 90/10, each having 3 mol percent of hexanediol dimethacrylate (HDDM) crosslinker. Three methods of forming the composite rods were utilized for this Example (A, B and C).

Method A utilized cores which were 6.0 mm (0.236 inches) in diameter. The cores were preswelled for 24 hours in HEMA. The tubes were suspended in a water bath ranging from 40° to 60° C. for 3 hours, held at 60° C. for 26.5 hours, removed from the bath, and further cured in a forced-air oven at 110° C. for 42 hours.

Method B utilized core rods of the 5 different mol ratios by allowing the cores to stand at 40° C. for 21 hours, prior to affecting cure by ramping the temperature to 60° C. This is equivalent to the standard cure conditions specified in Examples I-III and VI.

Method C utilized core rods prepared by the accelerated cure conditions as shown in Example VIII. In all three methods, the sheathing material is PMMA formulated as disclosed in the previous examples.

All samples were milled into rectangular slivers approximately 0.17 to 0.18 mm square, and 12 mm in length. Each sliver contained a blue (PMMA) and clear (hydrogel) region of unequal area. Both hydrated (distilled water) (Table 3) and nonhydrated (Table 4) specimens were pulled apart using a pull tester and both the force at break and the location of the break was noted.

The tensile strengths were determined by dividing the force at the break by the cross-sectional area. The break locations were divided into four regions: the blue PMMA region, the clear hydrogel region, the interfacial region (fragments contain both colors), and the interfacial line (all blue and all clear fragments).

TABLE 3
PULL TEST RESULTS - COMPOSITE MATERIAL
Hydrated in distilled water

| CORE SOLUTION p(HEMA-co-HOHEXMA) MOL RATIOS | CURE METHOD | TENSILE STRENGTH (kg/mm$^2$) | BREAK LOCATION | | |
|---|---|---|---|---|---|
| | | | PMMA REGION | INTERFACE LINE | INTERFACE REGION | HYDROGEL REGION |

| CORE SOLUTION p(HEMA-co-HOHEXMA) MOL RATIOS | CURE METHOD | TENSILE STRENGTH (kg/mm$^2$) | PMMA REGION | INTERFACE LINE | INTERFACE REGION | HYDROGEL REGION |
|---|---|---|---|---|---|---|
| 70/30 | A | 1.4 | 50.0% | 20.0% | 20.0% | 10.0% |
| 75/25 | A | 1.6 | 9.0% | 55.0% | 9.0% | 27.0% |
| 80/20 | A | 1.4 | 18.2% | 27.3% | 9.0% | 45.5% |
| 85/15 | A | 1.7 | 10.0% | 50.0% | 10.0% | 30.0% |
| 90/10 | A | 1.5 | 20.0% | 40.0% | 10.0% | 30.0% |
| 70/30 | B | 1.3 | 22.0% | 78.0% | — | — |
| 75/25 | B | 1.4 | — | 45.4% | 27.3% | 27.3% |
| 80/20 | B | 1.4 | 18.2% | 27.3% | 36.3% | 18.2% |
| 85/15 | B | 1.5 | 30.0% | 10.0% | 20.0% | 40.0% |
| 90/10 | C | 1.5 | 22.0% | 78.0% | — | — |
| 70/30 | C | 1.5 | 43.0% | — | 14.0% | 43.0% |
| 75/25 | C | 1.9 | — | 60.0% | 10.0% | 30.0% |
| 80/20 | C | 1.3 | 12.5% | 50.0% | 12.5% | 25.0% |
| 85/15 | C | 1.2 | 31.0% | 15.0% | 31.0% | 23.0% |
| 90/10 | C | 1.4 | 20.0% | 40.0% | 20.0% | 20.0% |

TABLE 4
PULL TEST RESULTS - COMPOSITE MATERIAL
Nonhydrated

| CORE SOLUTION p(HEMA-co-HOHEXMA) MOL RATIOS | CURE METHOD | TENSILE STRENGTH (kg/mm$^2$) | PMMA REGION | INTERFACE LINE | INTERFACE REGION | HYDROGEL REGION |
|---|---|---|---|---|---|---|
| 70/30 | A | 9.3 | 27.3% | 9.0% | 27.3% | 36.4% |
| 75/25 | A | 9.1 | 60.0% | — | 10.0% | 30.0% |
| 80/20 | A | 7.9 | 50.0% | — | 10.0% | 40.0% |
| 85/15 | A | 9.5 | 67.0% | — | — | 33.0% |
| 90/10 | A | 8.9 | 33.3% | — | 22.2% | 44.5% |
| 70/30 | B | 9.3 | 50.0% | — | — | 50.0% |
| 75/25 | B | 8.4 | 45.4% | — | 36.3% | 18.2% |
| 80/20 | B | 7.3 | 80.0% | — | 10.0% | 10.0% |
| 85/15 | B | 8.9 | 67.0% | — | — | 33.0% |
| 90/10 | C | 8.8 | 62.5% | 12.5% | 12.5% | 12.5% |
| 70/30 | C | 9.2 | 57.0% | — | — | 43.0% |
| 75/25 | C | 9.6 | 67.0% | — | 11.0% | 22.0% |
| 80/20 | C | 7.3 | 37.5% | — | 37.5% | 25.0% |
| 85/15 | C | 7.1 | 67.0% | — | 31.0% | 23.0% |
| 90/10 | C | 9.0 | 56.0% | — | 8.0% | 25.0% |

In the nonhydrated condition (Table 4), the tensile strength values are consistent with those expected for pure PMMA or nonhydrated hydrogel. Only a small percentage of the breaks occurred at the interfacial line, indicating that the adhesion of the two materials is excellent.

The tensile strength values of the hydrated slivers are much lower which is not unexpected as tensile strength of the hydrogel portions should decrease with increasing water content. However, no obvious decrease in tensile strength is seen between the various p(HEMAco-HOHEXMA) mol ratios. As can seen in Table 3, a greater percentage of failures occur at the interfacial line as compared to the dry specimens. This might be the result of stress brought about by the proximity of regions of vastly different aqueous expansion coefficient. However, the average tensile strength at break was not found to be significantly lower in specimens that broke at the interface line.

It should also be ruled that no major differences in tensile strength or in the location of break were noted between Method A, B or C of composite curing methods. Therefore, all 3 methods represent viable ways to prepare the composite intraocular lenses.

The embodiments above are intended to be illustrative of the invention, and it is expected that those of ordinary skill in the art may, in view of the teachings contained hereinabove, be able to modify the embodiments illustrated herein. It is intended to lower all such modifications which fell within the spirit and scope of the Invention as defined by the claims appended hereto.

What is claimed is:

1. A method for making a composite intraocular lens having a optic portion and a haptic portion, said method comprising the steps of:
   forming a core of a high refractive material suitable for use as an intraocular lens optic;
   swelling said core;
   polymerizing about said core a polymerizable material capable of forming said haptic portion to form an outer layer about said core, whereby said outer layer is bonded to said core, said outer layer and said core forming a composite rod; and
   machining said composite rod to form said composite intraocular lens having an optic portion and a haptic portion.

2. A method for making a composite intraocular lens having an optic portion and a haptic portion in accordance with claim 1, wherein said method further comprises the steps of:
   positioning said core in a mold; and
   placing said polymerizable material capable of forming said haptic portion of said composite intraocular lens in said mold about said core prior to polymerizing said polymerizable material.

3. A method for making a composite intraocular lens having an optic portion and a haptic portion in accordance with claim 1, wherein swelling of said core comprises applying a swelling agent to said core.

4. A method for making a composite intraocular lens having an optic portion and a haptic portion in accordance with claim 3, wherein said high refractive material suitable for use as an intraocular lens optic is poly(hydroxyethyl methacrylate), wherein said swelling agent is hydroxyethyl methacrylate, and wherein said polymerizable material capable of forming said haptic portion is poly(methyl methacrylate).

5. A method for making a composite intraocular lens having an optic portion and a haptic portion in accordance with claim 1, wherein swelling of said core comprises adding a polymerizable swelling agent to said polymerizable material capable of forming said haptic portion, said polymerizable swelling agent having a capacity to swell said core.

6. A method for making a composite intraocular lens having an optic portion and a haptic portion in accordance with claim 1, wherein swelling of said core comprises adding a comonomer of said high refractive material suitable for use as an intraocular lens optic to said high refractive material suitable for use as an intraocular lens optic, said comonomer having a capacity to induce swelling of said core when said polymerizable material capable of forming said haptic portion is polymerized.

7. A method for making a composite intraocular lens having an optic portion and a haptic portion in accordance with claim 1, wherein said high refractive material suitable for use as an intraocular lens optic is poly(hydroxyethyl methacrylate).

8. A method for making a composite intraocular lens having an optic portion and a haptic portion in accordance with claim 1, wherein said high refractive material suitable for use as an intraocular lens optic is selected from a group consisting of:
   poly(hydroxyethyl methacrylate);
   hydroxyethyl methacrylate/6-hydroxyhexyl methacrylate/ethylene glycol dimethacrylate; and
   hydroxyethyl methacrylate/6-hydroxyhexyl methacrylate/1,6-hexanediol dimethacrylate.

9. A method for making a composite intraocular lens having an optic portion and a haptic portion in accordance with claim 1, wherein said high refractive material suitable for use as an intraocular lens optic is selected from a group consisting of:
   hydroxyethyl methacrylate/N-vinylpyrrolidone;
   2,3-dihydroxypropyl methacrylate/methyl methacrylate;
   hydroxyethyl methacrylate/N-vinylpyrrolidone/methyl methacrylate;
   hydroxyethyl methacrylate/methacrylic acid;
   hydroxyethyl methacrylate/2-ethoxyethyl methacrylate;
   hydroxyethyl methacrylate/methacrylic acid/isobutyl methacrylate;
   hydroxypropyl methacrylamide/methyl methacrylate;
   hydroxyethyl methacrylate/n-butyl methacrylate;
   hydroxyethyl methacrylate/n-hexyl methacrylate;
   hydroxyethyl methacrylate/n-octyl methacrylate;
   hydroxyethyl methacrylate/hydroxyoctyl methacrylate;
   dimethyl acrylamide/diethyl acrylamide;
   hydroxyethyl methacrylate/n-hexyl acrylate; and
   hydroxyethyl methacrylate/hydroxypropyl methacrylate.

10. A method for making a composite intraocular lens having an optic portion and a haptic portion in accordance with claim 1, wherein said machining of said composite rod comprises cutting a disc from said composite rod and removing material from said outer layer of said composite rod to form at least one haptic portion of said composite intraocular lens.

11. A method for making a composite intraocular lens having an optic portion and a haptic portion in accordance with claim 1, wherein said method further comprises adding a polyfunctional crosslinking agent and an initiator to said high refractive material suitable for use as an intraocular lens optic and adding a polyfunctional crosslinking agent and an initiator to said polymerizable material capable of forming said haptic portion.

12. A method for making a composite intraocular lens having an optic portion and a haptic portion, said method comprising the steps of:
   forming a core of a high refractive material suitable for use as an intraocular lens optic, said high refractive material comprising a copolymer of hydroxyethyl methacrylate and a comonomer of hydroxyethyl methacrylate;

positioning said core in a mold;

placing a polymerizable material capable of forming said haptic portion of said composite intraocular lens in said mold about said core;

polymerizing said polymerizable material capable of forming said haptic portion to form an outer layer about said core, whereby said outer layer is bonded to said core, said outer layer and said core forming a one-piece rod; and machining said one-piece rod to form said composite intraocular lens having an optic portion and a haptic portion.

13. A method for making a composite intraocular lens having an optic portion and a haptic portion in accordance with claim 12, wherein said polymerizable material capable of forming said haptic portion is poly(methyl methacrylate).

14. A method for making a composite intraocular lens having an optic portion and a haptic portion in accordance with claim 12, wherein said monomer of hydroxyethyl methacrylate is 6-hydroxyhexyl methacrylate.

* * * * *